US008192752B2

(12) United States Patent
Tang et al.

(10) Patent No.: US 8,192,752 B2
(45) Date of Patent: Jun. 5, 2012

(54) COATINGS FOR IMPLANTABLE DEVICES INCLUDING BIOLOGICALLY ERODABLE POLYESTERS AND METHODS FOR FABRICATING THE SAME

(75) Inventors: Yiwen Tang, San Jose, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1689 days.

(21) Appl. No.: 10/719,516

(22) Filed: Nov. 21, 2003

(65) Prior Publication Data

US 2005/0112171 A1    May 26, 2005

(51) Int. Cl.
A61F 2/00              (2006.01)
(52) U.S. Cl. ............................................ 424/426
(58) Field of Classification Search .................. 424/426, 424/423, 424, 425; 623/1.1
See application file for complete search history.

(56) References Cited

U.S. PATENT DOCUMENTS

| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,329,383 A | 5/1982 | Joh .................... 428/36 |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz .................... 128/343 |
| 4,800,882 A | 1/1989 | Gianturco .................... 128/343 |
| 4,882,168 A | 11/1989 | Casey et al. .................... 424/468 |
| 4,886,062 A | 12/1989 | Wiktor .................... 128/343 |
| 4,931,287 A | 6/1990 | Bae et al. |
| 4,941,870 A | 7/1990 | Okada et al. .................... 600/36 |
| 4,977,901 A | 12/1990 | Ofstead .................... 128/772 |
| 5,019,096 A | 5/1991 | Fox, Jr. et al. |
| 5,100,992 A | 3/1992 | Cohn et al. |
| 5,112,457 A | 5/1992 | Marchant .................... 204/165 |
| 5,133,742 A | 7/1992 | Pinchuk |
| 5,163,952 A | 11/1992 | Froix |
| 5,165,919 A | 11/1992 | Sasaki et al. .................... 424/488 |
| 5,219,980 A | 6/1993 | Swidler |
| 5,258,020 A | 11/1993 | Froix |
| 5,272,012 A | 12/1993 | Opolski .................... 428/423.1 |
| 5,292,516 A | 3/1994 | Viegas et al. .................... 424/423 |
| 5,298,260 A | 3/1994 | Viegas et al. .................... 424/486 |
| 5,300,295 A | 4/1994 | Viegas et al. .................... 424/427 |
| 5,306,501 A | 4/1994 | Viegas et al. .................... 424/423 |
| 5,306,786 A | 4/1994 | Moens et al. |
| 5,328,471 A | 7/1994 | Slepian .................... 604/101 |
| 5,330,768 A | 7/1994 | Park et al. .................... 424/501 |
| 5,380,299 A | 1/1995 | Fearnot et al. .................... 604/265 |
| 5,417,981 A | 5/1995 | Endo et al. .................... 424/486 |
| 5,447,724 A | 9/1995 | Helmus et al. .................... 424/426 |
| 5,455,040 A | 10/1995 | Marchant .................... 424/426 |
| 5,462,990 A | 10/1995 | Hubbell et al. .................... 525/54.1 |
| 5,464,650 A | 11/1995 | Berg et al. .................... 427/2.3 |
| 5,485,496 A | 1/1996 | Lee et al. |
| 5,516,881 A | 5/1996 | Lee et al. |
| 5,569,463 A | 10/1996 | Helmus et al. .................... 424/426 |
| 5,578,073 A | 11/1996 | Haimovich et al. .................... 623/1 |
| 5,584,877 A | 12/1996 | Miyake et al. |
| 5,605,696 A | 2/1997 | Eury et al. .................... 424/423 |
| 5,607,467 A | 3/1997 | Froix |
| 5,609,629 A | 3/1997 | Fearnot et al. .................... 623/1 |
| 5,610,241 A | 3/1997 | Lee et al. |
| 5,616,338 A | 4/1997 | Fox, Jr. et al. |
| 5,624,411 A | 4/1997 | Tuch .................... 604/265 |
| 5,628,730 A | 5/1997 | Shapland et al. .................... 604/21 |
| 5,644,020 A | 7/1997 | Timmermann et al. |
| 5,649,977 A | 7/1997 | Campbell .................... 623/1 |
| 5,658,995 A | 8/1997 | Kohn et al. .................... 525/432 |
| 5,667,767 A | 9/1997 | Greff et al. .................... 424/9.411 |
| 5,670,558 A | 9/1997 | Onishi et al. .................... 523/112 |
| 5,674,242 A | 10/1997 | Phan et al. |
| 5,679,400 A | 10/1997 | Tuch .................... 427/2.14 |
| 5,700,286 A | 12/1997 | Tartaglia et al. .................... 623/1 |
| 5,702,754 A | 12/1997 | Zhong .................... 427/2.12 |
| 5,711,958 A | 1/1998 | Cohn et al. |
| 5,716,981 A | 2/1998 | Hunter et al. .................... 514/449 |
| 5,721,131 A | 2/1998 | Rudolph et al. |
| 5,723,219 A | 3/1998 | Kolluri et al. |
| 5,735,897 A | 4/1998 | Buirge .................... 623/12 |
| 5,746,998 A | 5/1998 | Torchilin et al. .................... 424/9.4 |

(Continued)

FOREIGN PATENT DOCUMENTS

| DE | 42 24 401 | 1/1994 |
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |

(Continued)

OTHER PUBLICATIONS

Polymeric Materials Encyclopedia, Salamone, J.C., 1996, CRC Press, Inc., p. 5687.*
Principles of Polymerization, 3$^{rd}$ ed., 1991, pp. 24-33.*
S. Montserrat et al. Polymer Bulletin 12, 173-180 (1984).*
Anonymous, *Cardiologists Draw—Up The Dream Stent*, Clinica 710:15 (Jun. 17, 1996), http://www.dialogweb.com/cgi/document?reg=1061848202959 printed Aug. 25, 2003 (2 pages).

(Continued)

*Primary Examiner* — James Rogers
(74) *Attorney, Agent, or Firm* — Squire Sanders (US) LLP

(57) ABSTRACT

A medical article comprising an implantable substrate having a coating is disclosed, the coating comprising a biologically erodable polymer having the glass transition temperature below about −50° C. The biologically erodable polymer can be blended with a polymeric additive which either has the glass transition temperature of about −50° C. or higher, or a degree of crystallinity greater than that of the first polymer.

27 Claims, 3 Drawing Sheets

U.S. PATENT DOCUMENTS

| | | | |
|---|---|---|---|
| 5,759,205 A | 6/1998 | Valentini | |
| 5,776,184 A | 7/1998 | Tuch | 623/1 |
| 5,783,657 A | 7/1998 | Pavlin et al. | |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,849,859 A | 12/1998 | Acemoglu | |
| 5,851,508 A | 12/1998 | Greff et al. | 424/9.411 |
| 5,854,376 A | 12/1998 | Higashi | |
| 5,858,746 A | 1/1999 | Hubbell et al. | 435/177 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,879,713 A | 3/1999 | Roth et al. | |
| 5,902,875 A | 5/1999 | Roby et al. | |
| 5,905,168 A | 5/1999 | Dos Santos et al. | |
| 5,910,564 A | 6/1999 | Gruning et al. | |
| 5,914,387 A | 6/1999 | Roby et al. | |
| 5,919,893 A | 7/1999 | Roby et al. | |
| 5,925,720 A | 7/1999 | Kataoka et al. | 525/523 |
| 5,932,299 A | 8/1999 | Katoot | |
| 5,955,509 A | 9/1999 | Webber et al. | 514/772.7 |
| 5,958,385 A | 9/1999 | Tondeur et al. | |
| 5,962,138 A | 10/1999 | Kolluri et al. | |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,001,117 A | 12/1999 | Huxel et al. | |
| 6,010,530 A | 1/2000 | Goicoechea | 623/1 |
| 6,011,125 A | 1/2000 | Lohmeijer et al. | |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,491 A | 9/2000 | Kohn et al. | |
| 6,120,536 A | 9/2000 | Ding et al. | 623/1.43 |
| 6,120,788 A | 9/2000 | Barrows | |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,136,333 A | 10/2000 | Cohn et al. | |
| 6,143,354 A | 11/2000 | Koulik et al. | |
| 6,153,252 A | 11/2000 | Hossainy et al. | 427/2.3 |
| 6,159,978 A | 12/2000 | Myers et al. | |
| 6,165,212 A | 12/2000 | Dereume et al. | 623/1.13 |
| 6,172,167 B1 | 1/2001 | Stapert et al. | |
| 6,177,523 B1 | 1/2001 | Reich et al. | |
| 6,180,632 B1 | 1/2001 | Myers et al. | |
| 6,203,551 B1 | 3/2001 | Wu | 606/108 |
| 6,211,249 B1 | 4/2001 | Cohn et al. | |
| 6,214,901 B1 | 4/2001 | Chudzik et al. | |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,245,760 B1 | 6/2001 | He et al. | |
| 6,248,129 B1 | 6/2001 | Froix | |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,258,371 B1 | 7/2001 | Koulik et al. | |
| 6,262,034 B1 | 7/2001 | Mathiowitz et al. | |
| 6,270,788 B1 | 8/2001 | Koulik et al. | |
| 6,274,164 B1 | 8/2001 | Novich | |
| 6,277,449 B1 | 8/2001 | Kolluri et al. | |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,344,035 B1 | 2/2002 | Chudzik et al. | |
| 6,346,110 B2 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,387,379 B1 | 5/2002 | Goldberg et al. | |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,482,834 B2 | 11/2002 | Spada et al. | |
| 6,494,862 B1 | 12/2002 | Ray et al. | 604/96.01 |
| 6,503,538 B1 | 1/2003 | Chu et al. | |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,524,347 B1 | 2/2003 | Myers et al. | |
| 6,527,801 B1 | 3/2003 | Dutta | 623/1.46 |
| 6,527,863 B1 | 3/2003 | Pacetti et al. | 118/500 |
| 6,528,526 B1 | 3/2003 | Myers et al. | |
| 6,530,950 B1 | 3/2003 | Alvarado et al. | |
| 6,530,951 B1 | 3/2003 | Bates et al. | |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,755 B2 | 7/2003 | Jackson et al. | |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,616,765 B1 | 9/2003 | Wu et al. | |
| 6,623,448 B2 | 9/2003 | Slater | |
| 6,625,486 B2 | 9/2003 | Lundkvist et al. | |
| 6,645,135 B1 | 11/2003 | Bhat | |
| 6,645,195 B1 | 11/2003 | Bhat et al. | |
| 6,656,216 B1 | 12/2003 | Hossainy | |
| 6,656,506 B1 | 12/2003 | Wu et al. | |
| 6,660,034 B1 | 12/2003 | Mandrusov et al. | |
| 6,663,662 B2 | 12/2003 | Pacetti et al. | |
| 6,663,880 B1 | 12/2003 | Roorda et al. | |
| 6,666,880 B1 | 12/2003 | Chiu et al. | |
| 6,673,154 B1 | 1/2004 | Pacetti et al. | |
| 6,673,385 B1 | 1/2004 | Ding et al. | |
| 6,689,099 B2 | 2/2004 | Mirzaee | |
| 6,695,920 B1 | 2/2004 | Pacetti et al. | |
| 6,703,040 B2 | 3/2004 | Katsarava et al. | |
| 6,706,013 B1 | 3/2004 | Bhat et al. | |
| 6,709,514 B1 | 3/2004 | Hossainy | |
| 6,712,845 B2 | 3/2004 | Hossainy | |
| 6,713,119 B2 | 3/2004 | Hossainy et al. | |
| 6,716,444 B1 | 4/2004 | Castro et al. | |
| 6,723,120 B2 | 4/2004 | Yan | |
| 6,733,768 B2 | 5/2004 | Hossainy et al. | |
| 6,740,040 B1 | 5/2004 | Mandrusov et al. | |
| 6,743,462 B1 | 6/2004 | Pacetti | |
| 6,749,626 B1 | 6/2004 | Bhat et al. | |
| 6,753,071 B1 | 6/2004 | Pacetti et al. | |
| 6,758,859 B1 | 7/2004 | Dang et al. | |
| 6,759,054 B2 | 7/2004 | Chen et al. | |
| 6,764,505 B1 | 7/2004 | Hossainy et al. | |
| 6,790,228 B2 | 9/2004 | Hossainy | |
| 6,818,063 B1 | 11/2004 | Kerrigan | |
| 6,824,559 B2 | 11/2004 | Michal | |

| | | |
|---|---|---|
| 2001/0007083 A1 | 7/2001 | Roorda |
| 2001/0014717 A1 | 8/2001 | Hossainy et al. |
| 2001/0018469 A1 | 8/2001 | Chen et al. .................. 523/121 |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. ......... 623/1.15 |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0077693 A1 | 6/2002 | Barclay et al. ............... 623/1.13 |
| 2002/0082679 A1 | 6/2002 | Sirhan et al. |
| 2002/0087123 A1 | 7/2002 | Hossainy et al. |
| 2002/0091433 A1 | 7/2002 | Ding et al. .................... 623/1.2 |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy ..................... 427/2.25 |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. ................. 623/1.13 |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman ..................... 424/486 |
| 2003/0104028 A1 | 6/2003 | Hossainy et al. |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti |
| 2004/0062853 A1 | 4/2004 | Pacetti et al. |
| 2004/0063805 A1 | 4/2004 | Pacetti |
| 2004/0071861 A1 | 4/2004 | Mandrusov |
| 2004/0072922 A1 | 4/2004 | Hossainy |
| 2004/0073298 A1 | 4/2004 | Hossainy |
| 2004/0086542 A1 | 5/2004 | Hossainy |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0180132 A1 | 9/2004 | Pacetti |
| 2004/0181271 A1 * | 9/2004 | DeSimone et al. ............ 623/1.1 |
| 2004/0191405 A1 | 9/2004 | Kerrigan |
| 2004/0253203 A1 | 12/2004 | Hossainy |
| 2005/0021127 A1 | 1/2005 | Kawula |
| 2005/0025799 A1 | 2/2005 | Hossainy |
| 2005/0074544 A1 | 4/2005 | Pacetti et al. |

FOREIGN PATENT DOCUMENTS

| | | |
|---|---|---|
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 0121229 A1 * | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |

OTHER PUBLICATIONS

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).
Matsumaru et al., *Embolic Materials for Endovascular Treatment of Cerebral Lesions*, J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Nordrehaug et al., *A novel biocompatible coating applied to coronary stents*, European Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).
Peng et al., *Role of polymers in improving the results of stenting in coronary arteries*, Biomaterials 17:685-694 (1996).
Shigeno, *Prevention of Cerebrovascular Spasm by Bosentan, Novel Endothelin Receptor*, Chemical Abstract 125:212307 (1996).
van Beusekom et al., *Coronary stent coatings*, Coronary Artery Disease 5(7):590-596 (Jul. 1994).
Wilensky et al., *Methods and Devices for Local Drug Delivery in Coronary and Peripheral Arteries*, Trends Cardiovasc. Med. 3(5):163-170 (1993).
Yokoyama et al., *Characterization of physical entrapment and chemical conjugation of adriamycin in polymeric micelles and their design for in vivo delivery to a solid tumor*, Journal of Controlled Release 50:79-92 (1998).
International Search Report and the Written Opinion for PCT/US2004/038951, filed Nov. 19, 2004, mailed Apr. 6, 2005, 12 pgs.
U.S. Appl. No. 09/406,473, filed Sep. 27, 1999, Pacetti.
U.S. Appl. No. 09/894,293, filed Jun. 27, 2001, Roorda et al.
U.S. Appl. No. 09/748,412, filed Dec. 21, 2000, Roorda.
U.S. Appl. No. 09/966,786, filed Sep. 27, 2001, Hossainy.
U.S. Appl. No. 09/967,632, filed Sep. 28, 2001, Pacetti.
U.S. Appl. No. 09/997,390, filed Nov. 30, 2001, Pacetti.
U.S. Appl. No. 10/040,538, filed Dec. 28, 2001, Pacetti et al.
U.S. Appl. No. 10/099,101, filed Mar. 15, 2002, Hossainy.
U.S. Appl. No. 10/104,179, filed Mar. 20, 2002, Ding.
U.S. Appl. No. 10/104,772, filed Mar. 20, 2002, Dutta.
U.S. Appl. No. 10/108,004, filed Mar. 27, 2002, Hossainy et al.
U.S. Appl. No. 10/176,510, filed Jun. 21, 2002, Hossainy et al.
U.S. Appl. No. 10/177,154, filed Jun. 21, 2002, Hossainy et al.
U.S. Appl. No. 10/176,504, filed Jun. 21, 2002, Roorda et al.
U.S. Appl. No. 10/177,117, filed Jun. 21, 2002, Hossainy.
U.S. Appl. No. 10/177,942, filed Jun. 21, 2002, Michal et al.
U.S. Appl. No. 10/199,272, filed Jul. 18, 2002, Ding.
U.S. Appl. No. 10/245,530, filed Sep. 17, 2002, Claude et al.
U.S. Appl. No. 10/246,883, filed Sep. 18, 2002, Taylor.
U.S. Appl. No. 10/255,911, filed Sep. 26, 2002, Ding.
U.S. Appl. No. 10/260,182, filed Sep. 27, 2002, Hossainy.
U.S. Appl. No. 10/262,150, filed Sep. 30, 2002, Limon.
U.S. Appl. No. 10/266,479, filed Oct. 8, 2002, Hossainy.
U.S. Appl. No. 10/271,851, filed Oct. 15, 2002, Roorda.
U.S. Appl. No. 10/286,058, filed Oct. 31, 2002, Pacetti et al.
U.S. Appl. No. 10/293,658, filed Nov. 12, 2002, Santos et al.
U.S. Appl. No. 10/316,739, filed Dec. 10, 2002, Zhang et al.
U.S. Appl. No. 10/319,042, filed Dec. 12, 2002, Sciver et al.
U.S. Appl. No. 10/327,371, filed Dec. 19, 2002, Lin et al.
U.S. Appl. No. 10/375,620, filed Feb. 26, 2003, Hossainy et al.
U.S. Appl. No. 10/375,496, filed Feb. 26, 2003, Esbeck.
U.S. Appl. No. 10/375,497, filed Feb. 26, 2003, Pacetti.
U.S. Appl. No. 10/376,027, filed Feb. 26, 2003, Kokish et al.
U.S. Appl. No. 10/376,348, filed Feb. 26, 2003, Ding et al.
U.S. Appl. No. 10/382,197, filed Mar. 4, 2003, Pacetti.
U.S. Appl. No. 10/428,691, filed May 1, 2003, Pacetti.
U.S. Appl. No. 10/438,378, filed May 15, 2003, Esbeck et al.
U.S. Appl. No. 10/606,711, filed Jun. 26, 2003, Pacetti.
U.S. Appl. No. 10/606,712, filed Jun. 26, 2003, Pacetti.
U.S. Appl. No. 10/630,250, filed Jul. 30, 2003, Pacetti et al.
U.S. Appl. No. 10/631,116, filed Jul. 31, 2003, Dehnad.
U.S. Appl. No. 10/705,546, filed Nov. 6, 2003, Kwok et al.
U.S. Appl. No. 10/714,111, filed Nov. 10, 2003, Claude.
Huang et al., *Biodegradable Polymers Derived from Aminoacids*, Macromol. Symp. 144, 7-32 (1999).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Saotome, et al., *Novel Enzymatically Degradable Polymers Comprising α-Amino Acid, 1,2-Ethanediol, and Adipic Acid*, Chemistry Letters, pp. 21-24, (1991).

* cited by examiner

COATINGS FOR IMPLANTABLE DEVICES INCLUDING BIOLOGICALLY ERODABLE POLYESTERS AND METHODS FOR FABRICATING THE SAME

BACKGROUND

1. Field of the Invention

This invention is directed to coatings for drug delivery devices, such as drug eluting vascular stents, and methods for producing the same.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Giant-urco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

Among the polymers that have been proposed to be used in stent coatings are biologically absorbable and/or biologically erodable polymers. It is expected that using biologically absorbable and/or biologically erodable polymers may eliminate or at least reduce a chronic adverse in vivo response that is sometimes present when non-absorbable and/or non-erodable polymers are used. However, the drug release properties of some biologically absorbable and/or biologically erodable polymers may be insufficient for some drugs. In other words, the drug may be released from the polymer too quickly. Accordingly, there is a great need for biologically absorbable and/or biologically erodable polymers that allow for the drug to reside at the treatment site for an effective duration of time.

SUMMARY

Figure 1:
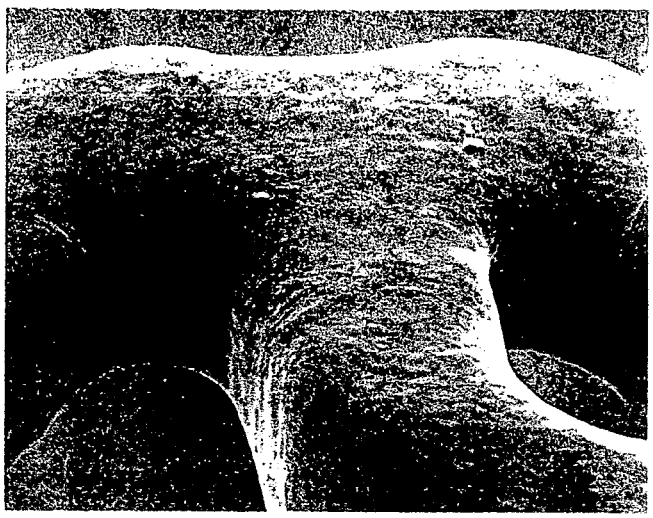
FIGS. 1 and 2 are microphotographs each showing a portion of a stent coated with a coatings according to embodiments of the present invention after the stimulated use test, as described by Examples.

A medical article comprising an implantable substrate having a coating is provided, the coating includes a first biologically erodable polymer having the glass transition temperature below about −50° C. The first polymer can include poly (esters), for example, poly(caprolactone), poly(4-hydroxybutyrate), poly(3-hydroxyvalerate), poly(3-hydroxybutyrate-co-3-hydroxyvalerate), and mixtures thereof. The coating can additionally include a biologically erodable polymeric additive mixed with the first polymer. According to one embodiment of the invention, the additive can be a polymer having the glass transition temperature of about −50° C. or greater. According to another embodiment of the invention, the additive can be a polymer having a degree of crystallinity greater than that of the first polymer. Examples of additives that can be used include poly(3-hydroxybutyrate), poly(L-lactide), poly(D,L-lactide), poly(L-lactide-co-D,L-lactide), poly(glycolide), poly(glycolide-co-L-lactide), poly(glycolide-co-D,L-lactide), poly (caprolactone-co-L-lactide), poly(caprolactone-co-D,L-lactide), poly(trimethylene carbonate), copolymers of trimethylenecarbonate, poly(orthoesters), tyrosine derived poly(carbonates), poly(iminocarbonates), poly(ester-amides), and mixtures thereof. According to one embodiment of the invention, the mass ratio between the first polymer and the additive can be between about 9:1 and about 0.16:1.

A method for fabricating a medical article is provided, the method includes depositing a coating on at least a portion of an implantable substrate, the coating including a first biologically erodable polymer having the glass transition temperature below about −50° C.

DETAILED DESCRIPTION

1. Terms and Definitions

The following definitions apply in the present invention:

The term "biologically erodable" refers to coatings and/or polymers that are capable of being eroded, dissolved and/or degraded when exposed to bodily fluids such as blood and are gradually resorbed, absorbed and/or eliminated by the body. The processes of breaking down and eventual absorption and elimination of the coating and/or polymer can be caused by, for example, hydrolysis, metabolic processes, bulk or surface erosion, and the like.

Whenever the reference is made to "biologically erodable" stent coatings and/or polymers forming such stent coatings, it is understood that after the process of degradation, erosion, absorption, and/or resorption has been completed, no biologically erodable polymer will remain on the stent. In some cases, a very insignificant trace or residue of the biologically erodable polymer may, however, remain on the stent. Whenever the term "biologically erodable" is used in this application, it is intended to broadly include biologically erodable, biologically dissolvable, biologically degradable, biologically absorbable, and biologically resorbable coatings and/or polymers.

The "glass transition temperature" ($T_g$) is defined as a temperature approximately in the middle of the temperature region where the onset of segmental motion in the chains of the polymer occurs leading to the eventual transition of the polymer from a glassy solid to an amorphous solid at atmospheric pressure. To restate in other words, $T_g$ is defined as an average temperature in the temperature region at which an amorphous polymer (or the amorphous regions in a partially crystalline polymer) changes from a hard and relatively brittle condition to a viscoelastic (rubbery) condition. In some embodiments, $T_g$ is intended to be the "average temperature" ±15° C., more narrowly, ±10° C. In some embodiments, $T_g$ falls within the "average temperature" ±5° C.

The "melting temperature" ($T_m$) of a polymer is defined as the temperature at which the last trace of crystallinity in a polymer disappears as a sample is exposed to increasing heat. The $T_m$ is always greater than the $T_g$ for a given polymer.

For the purposes of the present invention, the $T_g$ and $T_m$ for all polymers discussed below have been determined using the method of differential scanning calorimetry (DSC). DSC measures the change in heat capacity of a polymer as the polymer is exposed to an increasing temperature. When $T_g$ and $T_m$ of a polymer or a blend of polymers is measured using DSC, in some embodiments $T_g$ and/or $T_m$ are designed to fall within about ±15° C. of the measured temperature, more narrowly, within about ±10° C. of the measured temperature. In some embodiments $T_g$ and/or $T_m$ are designed to fall within about ±5° C. of the temperature measured by DSC.

The term or "degree of crystallinity" is defined as the fractional amount of crystalline phase in the polymer sample (by mass), assuming the sample can be subdivided into a crystalline phase and an amorphous phase. The phase is "crystalline" when a three-dimensional order on the level of atomic dimensions is present in the phase. The range of the three-dimensional order is below 50 nm in at least one direction. The degree of crystallinity can be determined by one or more of several experimental techniques, such as X-ray diffraction, calorimetry, density measurements, or infrared spectroscopy.

2. Embodiments of the Invention

A coating for an implantable medical device, such as a stent, according to embodiments of the present invention, can include any one or all of the following three layers:

(a) a primer layer;
(b) a drug-polymer layer (also referred to as "reservoir" or "reservoir layer") or alternatively a polymer free drug layer; and/or
(c) a topcoat layer.

Each layer of the stent coating can be formed on the stent by dissolving the polymer or a blend of polymers in a solvent, or a mixture of solvents, and applying the resulting polymer solution on the stent by spraying or immersing the stent in the solution. After the solution has been applied onto the stent, the coating is dried by allowing the solvent to evaporate. The process of drying can be accelerated if the drying is conducted at an elevated temperature.

To incorporate a drug into the reservoir layer, the drug can be combined with the polymer solution that is applied onto the stent as described above. Alternatively, to fabricate a polymer free drug layer, the drug can be dissolved in a suitable solvent or mixture of solvents, and the resulting drug solution can be applied on the stent by spraying or immersing the stent in the drug solution.

Instead of introducing the drug as a solution, the drug can be introduced as a colloidal system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. The suspension can be mixed with a polymer solution and the mixture can be applied on the stent as described above. Alternatively, the drug suspension can be applied on the stent without being mixed with the polymer solution.

The drug-polymer layer can be applied directly onto at least a part of the stent surface to serve as a reservoir for at least one active agent or a drug which is incorporated into the reservoir layer. The optional primer layer or polymer-free drug layer can be applied between the stent and the reservoir to improve the adhesion of the drug-polymer layer to the stent. The topcoat layer can be applied over at least a portion of the reservoir layer and serves as a rate limiting membrane which helps to control the rate of release of the drug. The topcoat layer can be essentially free from any active agents or drugs.

The process of the release of the drug from a coating having a topcoat layer includes at least two steps. First, the drug can diffuse into the polymer of the topcoat layer at the drug-polymer layer/topcoat layer interface. A change in concentration of drug across this interface can result from differences in drug solubility between the two layers. Next, the drug can diffuse through the topcoat layer via the free volume between the macromolecules of the topcoat layer polymer. Next, the drug can arrive at the outer surface of the topcoat layer, and desorb from the outer surface. At this point, the drug is released into the blood stream or tissue. Consequently, the topcoat layer can serve as a rate limiting barrier.

According to embodiments of the present invention, any of the aforementioned layers or regions in a coating can be made from a biologically erodable polymer. In some embodiments, the polymer is a polymeric blend. The polymeric blend comprises at least two polymers, each of which is a biologically erodable polymer. The composition of the blend in any of the layers can be the same or different. In some embodiments, only one of the layers can be made from a biologically erodable polymer or a blend, while the other layers can be made from other types of polymers. For example, the topcoat layer can be made from a biologically erodable polymer or a blend and the reservoir layer can be made from a conventional polymeric material or other sited materials.

The biologically erodable polymeric blend includes at least a principal polymer and a polymeric additive. In some embodiments, a bioabsorbable polyester having the glass transition temperature $T_g$ below about −50° C. can be used as the principal polymer. Examples of the principal polymers that can be used include poly(caprolactone) (PCL), poly(4-hydroxybutyrate), poly(3-hydroxyvalerate), grades of poly (3-hydroxybutyrate-co-3-hydroxyvalerate) having $T_g$ below about −50° C., and mixtures thereof. In some embodiments, the coating can be free from one particular principal polymer. For example, the coating can be free from PCL.

The polymeric additive in the biologically erodable polymeric blend is added to reduce the rate of release of a drug from a stent coating. The polymeric additive that can be used can have (a) either $T_g$ of about −50° C. or greater, or (b) a degree of crystallinity greater than that of the principal polymer, or both (a) and (b). In some embodiments, $T_g$ of the additive can be between about −50° C. and about 80° C., more narrowly, between about −20° C. and about 40° C., such as between about 0° C. and about 20° C.

An example of a polymeric additive that can be used is poly(3-hydroxybutyrate) having the formula —[O—CH(CH$_3$)—CH$_2$—C(O)—O]$_n$-(3-PHB). $T_g$ of 3-PHB is about 10° C., and $T_m$ is about 179° C. Molecular weight of 3-PHB can be within a range of between about 100,000 and about 500,000 Daltons. 3-PHB can be obtained from Aldrich Chemical Company of Milwaukee, Wis., or Goodfellow Corporation of Lancaster, Pa. Examples of other additives include poly(L-lactide), poly(D,L-lactide), poly(L-lactide-co-D,L-lactide), poly(glycolide), poly(glycolide-co-L-lactide), poly(glycolide-co-D,L-lactide), grades of poly(caprolactone-co-L-lactide) having $T_g$ of about −50° C. or higher, grades of poly(caprolactone-co-D,L-lactide) having $T_g$ of about −50° C. or higher, poly(trimethylene carbonate), copolymers of trimethylenecarbonate having $T_g$ of about −50° C. or higher, poly(orthoesters), tyrosine derived poly (carbonates), poly(iminocarbonates), poly(ester-amides), and mixtures thereof. In some embodiments, the coating can be free from any one of these additives.

The mass ratio between the principal polymer and the polymeric additive in the biologically erodable polymeric blend can be between about 9:1 and about 0.16:1, more narrowly, between about 6:1 and about 0.25:1, for example, between about 3:1 and about 0.33:1. One embodiment of the blend that can be used includes about 75 mass % PCL and the balance, 3-PHB. $T_g$ of such blend can be raised to about −47° C., compared to about −62° C. for pure PCL. The crystalline phases of the PCL and 3-PHB can both be present and retain distinct melting points. As a result, the elasticity of the polymeric material based on the blend can be lower than that of the pure PCL material depending on the degree of crystallinity of the samples.

As the crystallinity of 3-PHB is about 80% while that of PCL is about 57%, the crystallinity of the blend can be higher than that of the pure PCL material. Consequently, the reduction in rate of release of a drug from the stent coating can be anticipated for a stent coated with a PCL/3-PHB blend compared to a stent coated with pure PCL material based on the elevation of $T_g$ and potential increase in degree of crystallinity.

Any layer of the stent coating can contain any amount of the biologically erodable polymeric blend described above. If less than 100% of the layer is made of the biologically erodable polymeric blend, other, alternative, polymers can comprise the balance. While it is preferred that the alternative polymers be biodegradable, they may also be permanent or non-biodegradable. Examples of the alternative polymers that can be used include polyacrylates, such as poly(butyl methacrylate), poly(ethyl methacrylate), and poly(ethyl methacrylate-co-butyl methacrylate), and fluorinated polymers and/or copolymers, such as poly(vinylidene fluoride) and poly(vinylidene fluoride-co-hexafluoro propene), poly (N-vinyl pyrrolidone), polydioxanone, polyorthoester, polyanhydride, polyphosphoester, polyphosphoester urethane, poly(amino acids), cyanoacrylates, co-poly(ether-esters), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, vinyl halide polymers and copolymers (such as polyvinyl chloride), polyvinyl ethers (such as polyvinyl methyl ether), polyvinylidene chloride, polyacrylonitrile, polyvinyl ketones, polyvinyl aromatics (such as polystyrene), polyvinyl esters (such as polyvinyl acetate), copolymers of vinyl monomers with each other and olefins, e.g., poly(ethylene-co-vinyl alcohol) (EVAL), ethylene-methyl methacrylate copolymers, acrylonitrile-styrene copolymers, ABS resins, and ethylene-vinyl acetate copolymers; polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Representative examples of some solvents suitable for making the stent coatings include N,N-dimethylacetamide (DMAC), N,N-dimethylformamide (DMF), tetrahydrofurane (THF), cyclohexanone, xylene, toluene, acetone, i-propanol, methyl ethyl ketone, propylene glycol monomethyl ether, methyl butyl ketone, ethyl acetate, n-butyl acetate, and dioxane. Some solvent mixtures can be used as well. Representative examples of the mixtures include:

(1) DMAC and methanol (e.g., a 50:50 by mass mixture);
(2) water, i-propanol, and DMAC (e.g., a 10:3:87 by mass mixture);
(3) i-propanol, and DMAC (e.g., 80:20, 50:50, or 20:80 by mass mixtures);
(4) acetone and cyclohexanone (e.g., 80:20, 50:50, or 20:80 by mass mixtures);
(5) acetone and xylene (e.g. a 50:50 by mass mixture);
(6) acetone, FLUX REMOVER AMS, and xylene (e.g., a 10:50:40 by mass mixture); and
(7) 1,1,2-trichloroethane and chloroform (e.g., a 80:20 by mass mixture).

FLUX REMOVER AMS is trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance of methanol, with trace amounts of nitromethane. Those having ordinary skill in the art will select the solvent or a mixture of solvents suitable for a particular polymer being dissolved.

The therapeutic substance can include any substance capable of exerting a therapeutic or prophylactic effect for a patient. The therapeutic substance may include small molecule substances, peptides, proteins, oligonucleotides, and the like. The therapeutic substance could be designed, for example, to inhibit the activity of vascular smooth muscle cells. It can be directed at inhibiting abnormal or inappropriate migration and/or proliferation of smooth muscle cells to inhibit restenosis.

Examples of therapeutic substances that can be used include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany), methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.). Examples of cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

The coatings and methods of the present invention have been described with reference to a stent, such as a balloon expandable or self-expandable stent. The use of the coating is not limited to stents, however, and the coating can also be used with a variety of other medical devices. Examples of the medical device, that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

3. EXAMPLES

The following examples are provided to further illustrate embodiments of the present invention.

Example 1

A first composition was prepared by mixing the following components:
 (a) about 2.0 mass % poly(caprolactone) (PCL); and
 (b) the balance, a solvent blend, the blend comprising tetrahydrofuran (THF) and xylene in a mass ratio between THF and xylene of about 3:1.

The first composition was sprayed onto the surface of a bare 12 mm VISION stent (available from Guidant Corporation) and dried to form a stent coating. A spray coater was used having a 0.014 fan nozzle maintained at about 60° C. with a feed pressure of about 0.2 atm (about 3 psi) and an atomization pressure of about 1.3 atm (about 20 psi). The dry stent coating contained about 300 μg of PCL. To remove the solvent, the coating was baked at about 60° C. for about 2 hours.

The PCL coated stent was then subjected to a simulated use test. To test, an assembly comprising the PCL coated stent and a delivery catheter was made by crimping the stent on the catheter. The assembly was guided through a tortuous path and then deployed in a poly(vinyl alcohol) lesion having approximate size of about 3 by 10 millimeters. The tortuous path and the lesion contained de-ionized water at about 37° C. To deploy the stent, pressure of about 16 atm was applied to the balloon for about 1 minute, followed by deflating of the balloon and retraction of the catheter. After the catheter was retracted, de-ionized water was pumped through the tortuous path and the lesion for about 1 hour at a rate of about 50 milliliters per minute. Water was maintained at about 37° C. After 1 hour, the stent was removed from the poly(vinyl alcohol) lesion, dried, and prepared for analysis by scanning electron microscopy. An overall view of the stent after the simulated use test is shown by FIG. 1. As can be seen, the stent coating showed good mechanical integrity and the coating was uniform and smooth.

Example 2

A first composition was prepared by mixing the following components:
 (a) about 2.0 mass % PCL; and
 (b) the balance, a solvent blend, the blend comprising THF and xylene in a mass ratio between THF and xylene of about 3:1.

The first composition was sprayed onto the surface of a bare 12 mm VISION stent, dried and baked as described in Example 1 to form a dry primer layer. The dry primer layer contained about 100 μg of PCL.

A second composition was prepared by mixing the following components:
 (a) about 2.0 mass % EVEROLIMUS; and
 (b) the balance, a solvent blend, the blend comprising acetone and xylene in a mass ratio between acetone and xylene of about 3:2.

The second composition contained about 200 μg EVEROLIMUS. The second composition was applied onto the dried primer layer to form the reservoir layer.

A third composition was prepared by mixing the following components:
 (a) about 2.0 mass % PCL; and
 (b) the balance, a solvent blend, the blend comprising THF and xylene in a mass ratio between THF and xylene of about 3:1.

The third composition was sprayed onto the dry reservoir layer, dried and baked as described in Example 1, to form a dry topcoat layer. The dry topcoat layer contained about 400 μg of PCL.

Figure 2:

The coated stent was then subjected to a simulated use test described above. An overall view of the stent after the simulated use test is shown by FIG. 2. As can be seen, the stent coating showed good mechanical integrity and the coating was uniform and smooth.

Example 3

Figure 3:
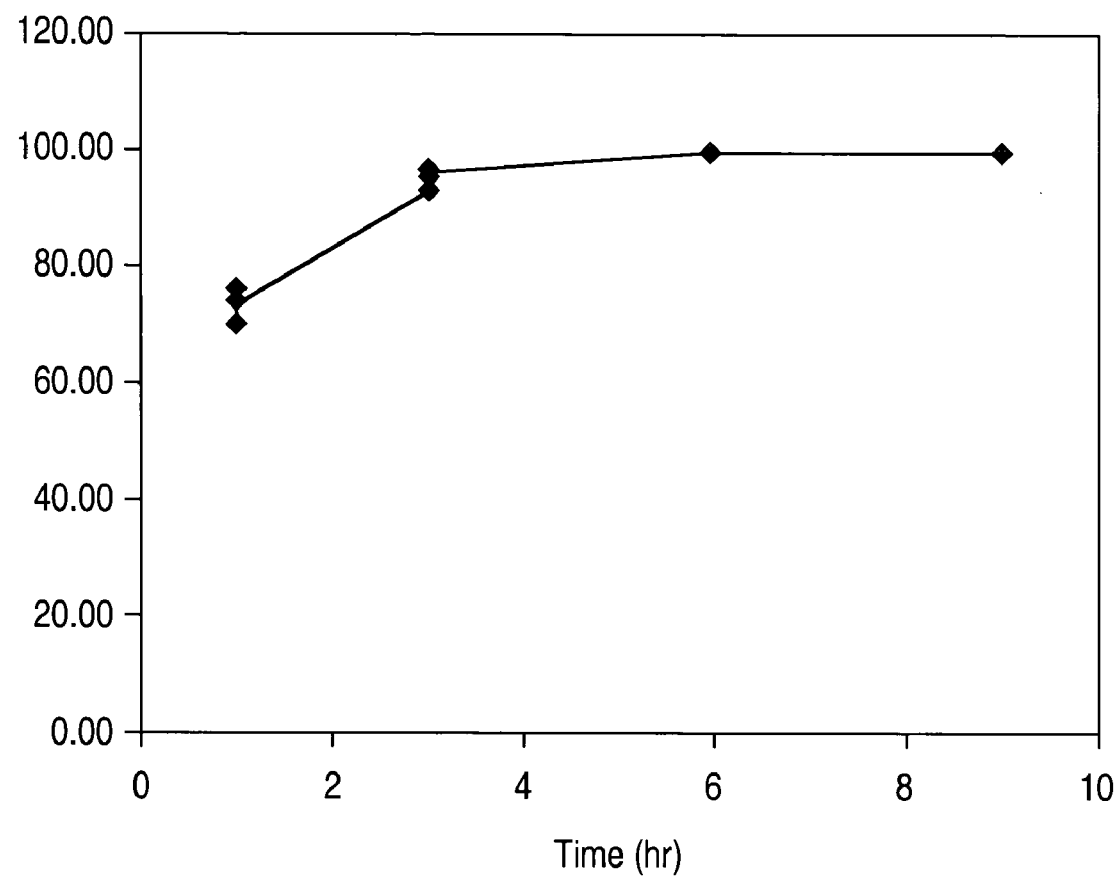
FIG. 3 is a chart showing a profile of release of a drug from a stent coating fabricated according to an embodiment of the present invention.

The stent coating made as described in Example 2 was also tested for drug release. The stent was immersed in an aqueous solution containing about 1 mass % TRITON X-100 surfactant. TRITON is trade name of a condensate of p-octylphenol with ethylene oxide registered to Rohm & Haas Co. and available from Aldrich Co. The solution was maintained at a temperature of about 37° C., and the drug release was measured by assaying the solution using the high pressure liquid chromatography (HPLC) method after 1, 3, 6, and 9 hours, while the temperature of the solution was maintained constant at about 37° C. As shown by the graph presented by FIG. 3, essentially the entire amount of EVEROLIMUS was released within 6 hours.

Example 4

A first composition was prepared by mixing the following components:
(a) about 2.0 mass % poly(3-hydroxybutyrate) (3-PHB); and
(b) the balance, a solvent blend, the blend comprising 1,1,2-trichloroethane (TCE) and chloroform in a mass ratio between TCE and chloroform of about 4:1.

The first composition was sprayed onto the surface of a bare 12 mm VISION stent, dried and baked as described in Example 1 to form a stent coating.

Figure 4:
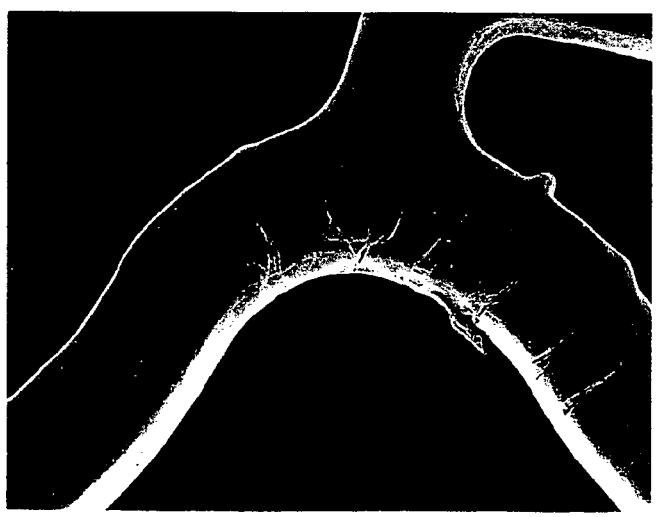
FIGS. 4-7 are microphotographs each showing a portion of a stent coated with a coatings according to embodiments of the present invention after the wet expansion test, as described by Examples.

The stent coated with 3-PHB was then subjected to a wet expansion test. To test, an assembly comprising the coated stent and a delivery catheter was made by crimping the stent on the catheter, followed by immersion in de-ionized water, which was maintained at about 37° C. The stent was expanded while wet, followed by deflating the catheter, removing and drying the stent. An overall view of the stent after the wet expansion test is shown by FIG. 4. As can be seen, the stent coating has developed cracks at the high strain joints.

Example 5

A primer and reservoir layers were formed on a 12 mm VISION stent as described in Example 2. A composition was then prepared by mixing the following components:
(a) about 0.75 mass % PCL;
(b) about 0.25 mass % 3-PHB; and
(c) the balance, a solvent blend, the blend comprising TCE and chloroform in a mass ratio between TCE and chloroform of about 4:1.

The composition was sprayed onto the dry reservoir layer, dried and baked, to form a dry topcoat layer. The dry topcoat layer contained about 400 μg of the PCL/3-PHB mixture.

Figure 5:

The coated stent was then subjected to a wet expansion test described in Example 4. An overall view of the stent after the wet expansion test is shown by FIG. 5. As can be seen, the stent coating showed good mechanical integrity. The coating was uniform and smooth.

Example 6

A primer and reservoir layers were formed on a 12 mm VISION stent as described in Example 2. A composition was then prepared by mixing the following components:
(a) about 0.5 mass % PCL;
(b) about 0.5 mass % 3-PHB; and
(c) the balance, a solvent blend, the blend comprising TCE and chloroform in a mass ratio between TCE and chloroform of about 4:1.

The composition was sprayed onto the dry reservoir layer, dried and baked as described in Example 1, to form a dry topcoat layer. The dry topcoat layer contained about 400 μg of the PCL/3-PHB mixture.

Figure 6:

The coated stent was then subjected to a wet expansion test described in Example 4. An overall view of the stent after the wet expansion test is shown by FIG. 6. As can be seen, the stent coating showed good mechanical integrity and the coating was uniform and smooth.

Example 7

A primer and reservoir layers were formed on a 12 mm VISION stent as described in Example 2. A composition was then prepared by mixing the following components:
(a) about 0.25 mass % PCL;
(b) about 0.75 mass % 3-PHB; and
(c) the balance, a solvent blend, the blend comprising TCE and chloroform in a mass ratio between TCE and chloroform of about 4:1.

The composition was sprayed onto the dry reservoir layer, dried and baked, to form a dry topcoat layer. The dry topcoat layer contained about 400 μg of the PCL/3-PHB mixture.

Figure 7:

The coated stent was then subjected to a wet expansion test described in Example 4. An overall view of the stent after the wet expansion test is shown by FIG. 7. As can be seen, the stent coating showed good mechanical integrity. The coating was uniform and smooth.

Example 8

The stents were additionally assayed for drug release. The stents were immersed in stirred porcine serum at about 37° C. for about 24 hours to simulate an in vivo environment. The stents coated according to Examples 2, 4, 5, and 6 were used. The amount of the drug remaining on the stent was measured using HPLC. The results are summarized in Table 1.

TABLE 1

| | | Drug Release in Porcine Serum | | | |
|---|---|---|---|---|---|
| No. | Stent Of Example No. | Primer | Reservoir | Topcoat | EVEROLIMUS Released After 24 Hours in Porcine Serum, % |
| 1 | 2 | PCL, 100 μg | EVEROLIMUS, 200 μg | PCL, 400 μg | 100 |

TABLE 1-continued

Drug Release in Porcine Serum

| No. | Stent Of Example No. | Primer | Reservoir | Topcoat | EVEROLIMUS Released After 24 Hours in Porcine Serum, % |
|---|---|---|---|---|---|
| 3 | 6 | PCL, 100 µg | EVEROLIMUS, 200 µg | PCL/3-PHB, 400 µg (PCL/3-PHB ratio is 1:1) | 72 |
| 4 | 7 | PCL, 100 µg | EVEROLIMUS, 200 µg | PCL/3-PHB, 400 µg (PCL/3-PHB ratio is 1:3) | 37 |

As seen from Table 1, after exposure to the porcine serum, the entire amount of EVEROLIMUS was released within 24 hours from the stent of Example 2, which had no 3-PHB in the topcoat. At the same time, the stent coated with a 3-PHB-containing coating released substantially smaller amount of the drug after 24 hour exposure.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical article comprising an implantable substrate having a coating, the coating comprising a first biologically erodable polymer having a glass transition temperature below about −50° C. and a biologically erodable polymeric additive mixed with the first polymer, wherein:
    the polymeric additive has a degree of crystallinity greater than that of the first polymer and has a glass transition temperature of about −50° C. or greater;
    the first polymer is selected from poly(esters), poly(caprolactone), poly(4-hydroxybutyrate), poly(3-hydroxyvalerate), poly(3-hydroxybutyrate-co-3-hydroxyvalerate), and mixtures thereof; and
    the polymeric additive is selected from poly(L-lactide), poly(L-lactide-co-D,L-lactide), poly(glycolide), poly(glycolide-co-L-lactide), poly(caprolactone-co-L-lactide), poly(caprolactone-co-D,L-lactide), copolymers of trimethylene carbonate, and mixtures thereof.

2. The medical article of claim 1, wherein the first polymer includes poly(esters).

3. The medical article of claim 1, wherein the first polymer is poly(caprolactone).

4. The medical article of claim 1, wherein the first polymer is selected from a group consisting of poly(4-hydroxybutyrate), poly(3-hydroxyvalerate), poly(3-hydroxybutyrate-co-3-hydroxyvalerate), and mixtures thereof.

5. The medical article of claim 1, wherein the additive is a polymer having the glass transition temperature between about −50° C. and about 80° C.

6. The medical article of claim 1, wherein the additive is a polymer having the glass transition temperature between about −20° C. and about 40° C.

7. The medical article of claim 1, wherein the additive is a polymer having the glass transition temperature between about 0° C. and about 20° C.

8. The medical article of claim 1, wherein the medical article is a stent.

9. The medical article of claim 1, wherein the mass ratio between the first polymer and the polymeric additive is between about 9:1 and about 0.16:1.

10. The medical article of claim 1, wherein the mass ratio between the first polymer and the polymeric additive is between about 6:1 and about 0.25:1.

11. The medical article of claim 1, wherein the mass ratio between the first polymer and the polymeric additive is between about 3:1 and about 0.33:1.

12. The medical article of claim 1, wherein the coating additionally comprises a therapeutic substance.

13. The medical article of claim 1, wherein the coating is a topcoat layer disposed over a drug reservoir layer for reducing the rate of release of a drug from the reservoir layer.

14. A method for fabricating a medical article, the method including depositing a coating on at least a portion of an implantable substrate, the coating including a first biologically erodable polymer having a glass transition temperature below about −50° C. and a biologically erodable polymeric additive mixed with the first polymer, wherein:
    the polymeric additive has a degree of crystallinity greater than that of the first polymer and has a glass transition temperature of about −50° C. or greater;
    the first polymer is selected from poly(esters), poly(caprolactone), poly(4-hydroxybutyrate), poly(3-hydroxyvalerate), poly(3-hydroxybutyrate-co-3-hydroxyvalerate), and mixtures thereof; and
    the polymeric additive is selected from poly(L-lactide), poly(L-lactide-co-D, L-lactide), poly(glycolide), poly(glycolide-co-L-lactide), poly(caprolactone-co-L-lactide), poly(caprolactone-co-D,L-lactide), copolymers of trimethylene carbonate, and mixtures thereof.

15. The method of claim 14, wherein the first polymer includes poly(esters).

16. The method of claim 14, wherein the first polymer is poly(caprolactone).

17. The method of claim 14, wherein the first polymer is selected from a group consisting of poly(4-hydroxybutyrate), poly(3-hydroxyvalerate), poly(3-hydroxybutyrate-co-3-hydroxyvalerate), and mixtures thereof.

18. The method of claim 14, wherein the additive is a polymer having the glass transition temperature between about −50° C. and about 80° C.

19. The method of claim 14, wherein the additive is a polymer having the glass transition temperature between about −20° C. and about 40° C.

20. The method of claim 14, wherein the additive is a polymer having the glass transition temperature between about 0° C. and about 20° C.

21. The method of claim 14, wherein the medical article is a stent.

22. The method of claim 14, wherein the mass ratio between the first polymer and the polymeric additive is between about 9:1 and about 0.16:1.

23. The method of claim 14, wherein the mass ratio between the first polymer and the polymeric additive is between about 6:1 and about 0.25:1.

24. The method of claim 14, wherein the mass ratio between the first polymer and the polymeric additive is between about 3:1 and about 0.33:1.

25. The method of claim 14, wherein the coating additionally comprises a therapeutic substance.

26. The medical article of claim 1, wherein the polymeric additive comprises poly(L-lactide).

27. The medical article of claim 14, wherein the polymeric additive comprises poly(L-lactide).

* * * * *

UNITED STATES PATENT AND TRADEMARK OFFICE
CERTIFICATE OF CORRECTION

PATENT NO. : 8,192,752 B2
APPLICATION NO. : 10/719516
DATED : June 5, 2012
INVENTOR(S) : Tang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1851 days.

Signed and Sealed this
Seventeenth Day of March, 2020

Andrei Iancu
*Director of the United States Patent and Trademark Office*